(12) United States Patent
Mollov et al.

(10) Patent No.: US 11,071,514 B2
(45) Date of Patent: Jul. 27, 2021

(54) IMAGING SYSTEM WITH ENERGY SENSING AND METHOD FOR OPERATION

(71) Applicant: Varex Imaging Corporation, Salt Lake City, UT (US)

(72) Inventors: Ivan P. Mollov, Mountain View, CA (US); Arundhuti Ganguly, San Jose, CA (US)

(73) Assignee: Varex Imaging Corporation, Salt Lake City, UT (US)

( * ) Notice: Subject to any disclaimer, the term of this patent is extended or adjusted under 35 U.S.C. 154(b) by 0 days.

(21) Appl. No.: 16/192,917

(22) Filed: Nov. 16, 2018

(65) Prior Publication Data

US 2020/0155110 A1    May 21, 2020

(51) Int. Cl.
*A61B 6/00* (2006.01)
*G01T 1/24* (2006.01)
*G01T 7/00* (2006.01)

(52) U.S. Cl.
CPC ............ *A61B 6/585* (2013.01); *A61B 6/4233* (2013.01); *A61B 6/4241* (2013.01); *A61B 6/4283* (2013.01); *A61B 6/482* (2013.01); *A61B 6/542* (2013.01); *A61B 6/545* (2013.01); *G01T 1/24* (2013.01); *G01T 7/005* (2013.01)

(58) Field of Classification Search
CPC ....... A61B 6/42; A61B 6/4208; A61B 6/4233; A61B 6/4241; A61B 6/4283; A61B 6/482; A61B 6/54; A61B 6/542; A61B 6/545; A61B 6/58; A61B 6/582; A61B 6/585; G01T 1/24
USPC ........... 378/62, 98.7, 98.8, 98.9, 98.11, 207; 250/370.09
See application file for complete search history.

(56) References Cited

U.S. PATENT DOCUMENTS

| | | | | |
|---|---|---|---|---|
| 5,943,388 A * | 8/1999 | Turner | ................ | G01V 5/0041 378/98.11 |
| 6,784,433 B2 * | 8/2004 | Zur | ..................... | G01T 1/2018 250/370.08 |
| 7,092,481 B2 * | 8/2006 | Hoffman | ............ | A61B 6/4241 250/370.09 |
| 7,149,278 B2 * | 12/2006 | Arenson | ............. | A61B 6/4241 378/19 |
| 7,209,536 B2 * | 4/2007 | Walter | .................. | A61B 6/032 378/5 |

(Continued)

FOREIGN PATENT DOCUMENTS

| | | |
|---|---|---|
| JP | 2008-309683 | 12/2008 |
| JP | 2016-223952 | 12/2016 |
| WO | 2016194315 | 12/2016 |

OTHER PUBLICATIONS

PCT/US2019/058814, International Search Report dated Feb. 20, 2020.

(Continued)

*Primary Examiner* — Allen C. Ho
(74) *Attorney, Agent, or Firm* — Laurence & Phillips IP Law

(57) ABSTRACT

Some embodiments include a system, comprising: an integrating detector including a plurality of pixels, each pixel configured to integrate signal from photons of a radiation beam; and an energy sensing detector overlapping the plurality of pixels of the integrating detector and configured to generate energy information in response to the radiation beam.

20 Claims, 11 Drawing Sheets

(56) References Cited

U.S. PATENT DOCUMENTS

| | | | |
|---|---|---|---|
| 7,260,174 B2 * | 8/2007 | Hoffman | A61B 6/032 250/363.09 |
| 7,263,167 B2 * | 8/2007 | Walter | A61B 6/032 378/116 |
| 7,480,362 B2 * | 1/2009 | Carmi | A61B 6/032 378/19 |
| 7,486,764 B2 * | 2/2009 | Tkaczyk | G01T 1/249 250/370.09 |
| 7,488,945 B2 * | 2/2009 | Li | G01T 1/2928 250/370.09 |
| 7,532,703 B2 * | 5/2009 | Du | A61B 6/032 378/116 |
| 7,573,040 B2 * | 8/2009 | Tkaczyk | G01T 1/249 250/370.09 |
| 7,606,346 B2 * | 10/2009 | Tkaczyk | A61B 6/032 250/370.09 |
| 7,606,347 B2 * | 10/2009 | Tkaczyk | A61B 6/032 378/19 |
| 7,626,172 B2 | 12/2009 | Takahashi et al. | |
| 7,709,803 B2 * | 5/2010 | Adachi | G01T 1/244 250/370.09 |
| 7,782,383 B2 * | 8/2010 | Olsen | H04N 5/357 250/208.1 |
| 7,894,576 B2 * | 2/2011 | Carmi | G01T 1/2985 378/98.9 |
| 7,991,106 B2 * | 8/2011 | Ren | A61B 6/585 378/37 |
| 8,373,135 B2 * | 2/2013 | Kappler | G01T 1/247 250/336.1 |
| 8,378,310 B2 * | 2/2013 | Bornefalk | G06T 11/005 250/370.09 |
| 8,426,828 B2 * | 4/2013 | Dierickx | G01J 1/44 250/371 |
| 8,442,184 B2 * | 5/2013 | Forthmann | A61B 6/032 378/5 |
| 8,513,614 B2 * | 8/2013 | Kraft | G01T 1/1647 250/370.09 |
| 8,619,943 B2 * | 12/2013 | Flohr | A61B 6/032 378/19 |
| 8,891,845 B2 * | 11/2014 | Ogawa | G06T 3/0031 382/128 |
| 8,958,524 B2 * | 2/2015 | Subramanian | G01N 23/046 378/4 |
| 9,044,189 B2 * | 6/2015 | Flohr | A61B 6/032 |
| 9,234,967 B2 * | 1/2016 | Batkilin | G01T 1/20 |
| 9,289,184 B2 * | 3/2016 | Lalena | A61B 6/5205 |
| 9,351,701 B2 * | 5/2016 | Yamakawa | A61B 6/025 |
| 9,389,320 B2 * | 7/2016 | Ogawa | A61B 6/14 |
| 9,417,339 B2 * | 8/2016 | Spahn | A61B 6/4241 |
| 9,488,739 B2 * | 11/2016 | Pelc | G01T 1/247 |
| 9,517,045 B2 * | 12/2016 | Kang | G01N 23/087 |
| 9,530,196 B2 | 12/2016 | Mishin | |
| 9,532,759 B2 * | 1/2017 | Taguchi | A61B 6/032 |
| 9,588,235 B2 | 3/2017 | Weisfield et al. | |
| 9,610,055 B2 * | 4/2017 | Taguchi | A61B 6/5205 |
| 9,750,471 B2 * | 9/2017 | Schirra | G01T 1/161 |
| 9,854,656 B2 * | 12/2017 | Göderer et al. | A61B 6/4241 |
| 9,867,580 B2 * | 1/2018 | Danielsson | H04N 5/3745 |
| 9,867,590 B2 * | 1/2018 | Tamura | H01J 35/14 |
| 9,872,661 B2 * | 1/2018 | Ono | A61B 6/4241 |
| 10,001,567 B2 * | 6/2018 | Roessl | G01T 7/005 |
| 10,034,652 B2 * | 7/2018 | Cho | A61B 6/585 |
| 10,117,626 B2 * | 11/2018 | Fu | A61B 6/4208 |
| 10,117,628 B2 * | 11/2018 | Tamura | A61B 6/482 |
| 10,154,821 B2 * | 12/2018 | Kawata | A61B 6/585 |
| 10,159,450 B2 * | 12/2018 | Kato | A61B 6/4208 |
| 10,217,246 B2 * | 2/2019 | Takayama | A61B 6/032 |
| 10,274,608 B2 * | 4/2019 | Schroeter | G01T 7/005 |
| 10,281,596 B2 * | 5/2019 | Daerr | G01T 1/24 |
| 10,448,914 B2 * | 10/2019 | Spahn | H04N 5/335 |
| 10,485,503 B2 * | 11/2019 | Schaefer | G01T 1/2985 |
| 10,507,005 B2 * | 12/2019 | Jin | G01T 7/005 |
| 10,575,800 B2 * | 3/2020 | Danielsson | G01B 15/045 |
| 10,575,801 B2 * | 3/2020 | Danielsson | G01T 1/17 |
| 10,610,191 B2 * | 4/2020 | Sjolin | A61B 6/585 |
| 10,631,800 B2 * | 4/2020 | Siewerdsen | A61B 6/4007 |
| 10,660,589 B2 * | 5/2020 | Roessl | A61B 6/4233 |
| 10,725,188 B2 * | 7/2020 | Steadman Booker | G01T 1/247 |
| 10,743,826 B2 * | 8/2020 | Cao | A61B 6/4275 |
| 10,743,834 B2 * | 8/2020 | Kato | A61B 6/54 |
| 10,952,697 B2 * | 3/2021 | Lalena | A61B 6/465 |
| 2012/0025086 A1 | 2/2012 | Takihi | |
| 2014/0077086 A1 | 3/2014 | Batkilin et al. | |

OTHER PUBLICATIONS

PCT/US2019/058814, Written Opinion of International Search Authority dated Feb. 20, 2020.

* cited by examiner

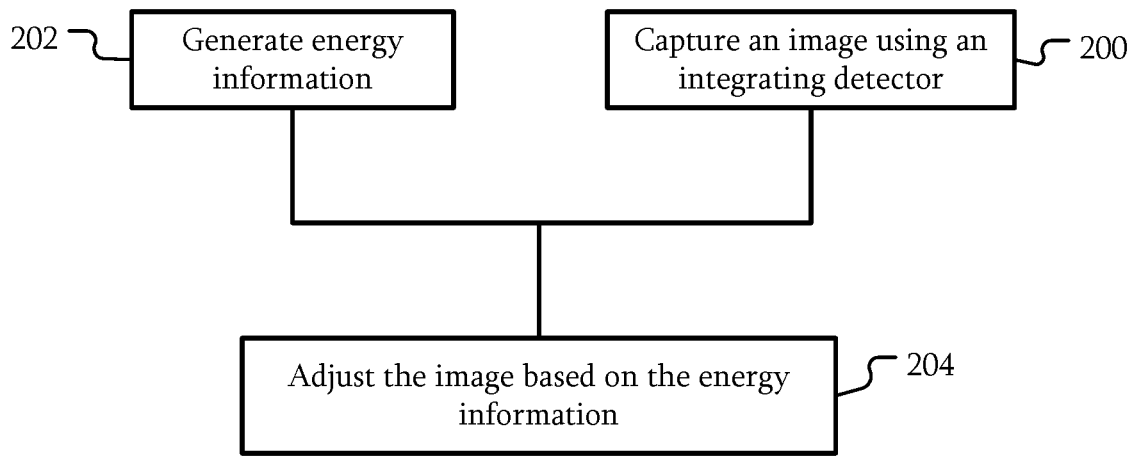
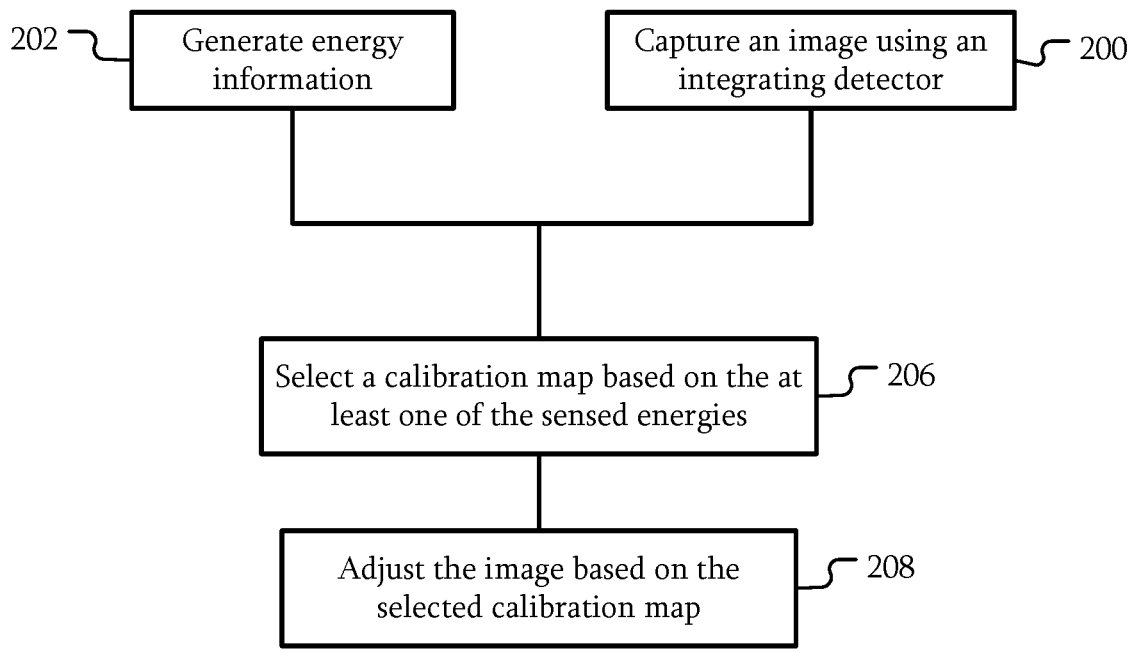

IMAGING SYSTEM WITH ENERGY SENSING AND METHOD FOR OPERATION

BACKGROUND

X-ray imaging detectors include matrix electronic devices that convert a two-dimensional (2D) x-ray distribution into a digital computer image showing features of an object, such as the internal organs of a patient under examination, a vehicle during cargo scanning, or the like. 2D x-ray imagers in production have integrating circuitry in the pixels that produces a signal proportional to the total x-ray exposure at the pixel site. X-ray photons with different energy contribute to the total signal in every pixel, but because the total signal in every pixel is a sum of the signals from all x-ray photons, the energy information from the different x-ray photons is lost.

BRIEF DESCRIPTION OF SEVERAL VIEWS OF THE DRAWINGS

FIG. 2A-2E are flowcharts illustrating operation an imaging system according to some embodiments.

DETAILED DESCRIPTION

This disclosure relates to imaging systems and, in particular, to imaging systems with integrating and energy sensing detectors.

Sensitivity variation across an imaging device may be dependent on the energy distribution or the average energy of the illumination. For example, with an X-ray imager matrix, the sensitivity across the imager may vary based on the energy of the x-ray beam. This leads to image artifacts when gain calibration uses one average energy of the x-ray beam and object imaging results in different average energy at the imager. Because an integrating detector circuitry loses the energy information of individual photons, the energy distribution, the average energy, or the peak energy of the x-ray beam may not be available to the imaging system. U.S. Pat. Nos. 7,782,383 and 8,426,828 describe examples of energy integrating detectors and energy sensing detectors. However, as will be described in further detail below, in some embodiments, the variation may be reduced or eliminated by performing gain calibrations at multiple separate energies and choosing which calibration to use depending on energy information associated with the actual x-ray beam at the imager for any particular examination.

Figure 1A:
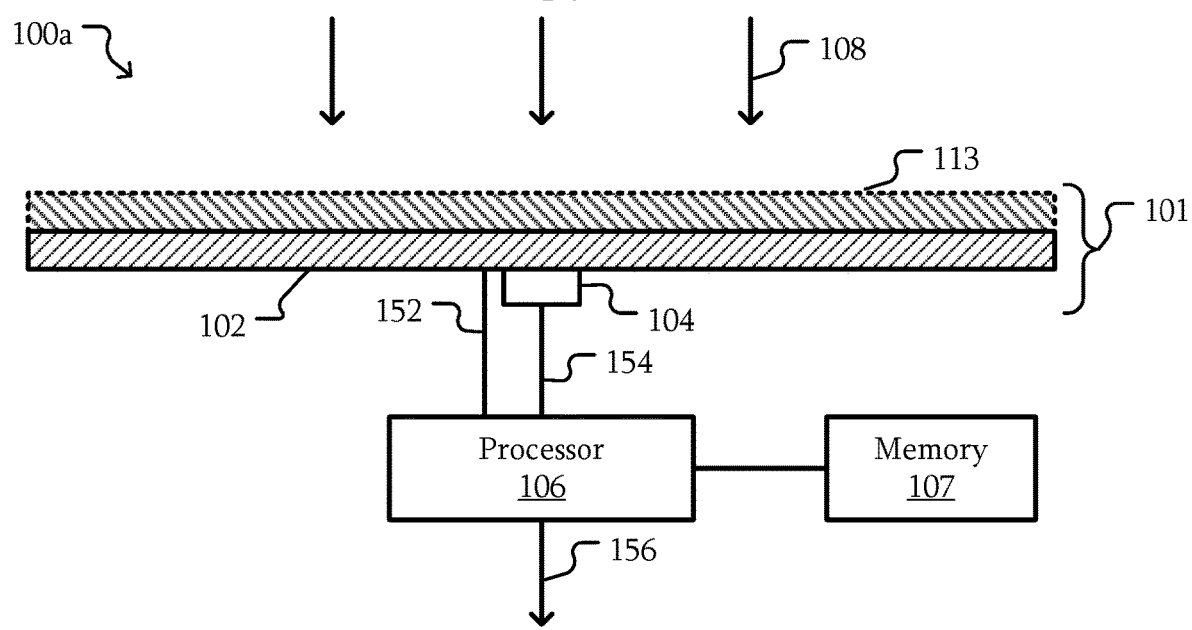
FIG. 1A is a block diagram of an imaging system according to some embodiments.
Figure 1B:
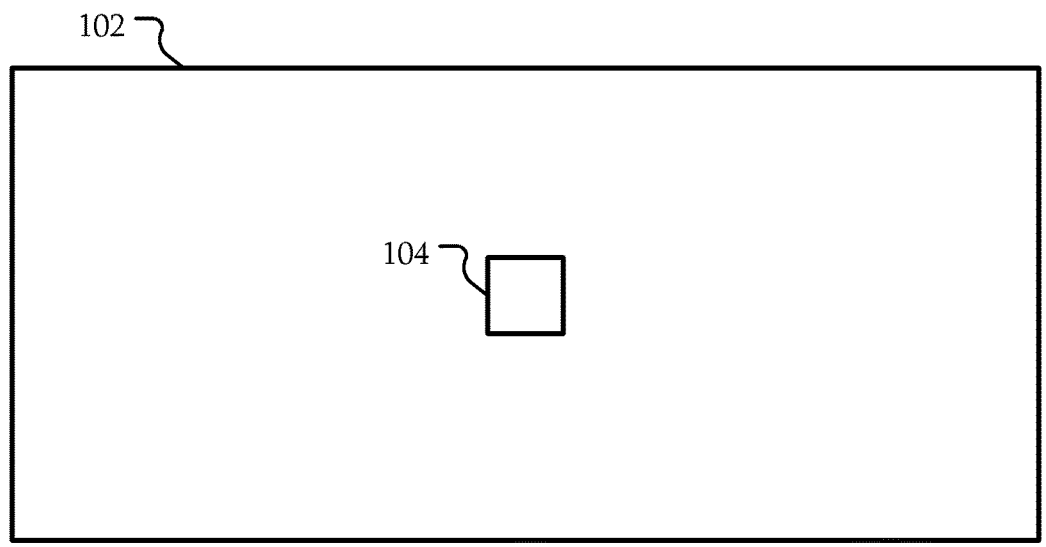
FIG. 1B is a plan view of detectors of the imaging system of FIG. 1A according to some embodiments.

FIG. 1A is a block diagram of an imaging system 100a according to some embodiments. FIG. 1B is a plan view of detectors of the imaging system of FIG. 1A according to some embodiments. One or more of imaging systems 100a-100h may be referred to as imaging systems 100. Referring to FIGS. 1A and 1B, the imaging system 100a includes a detector 101 including an integrating detector 102 and an energy sensing detector 104. The integrating detector 102 and energy sensing detector 104 are coupled to a processor 106.

Figure 1C:
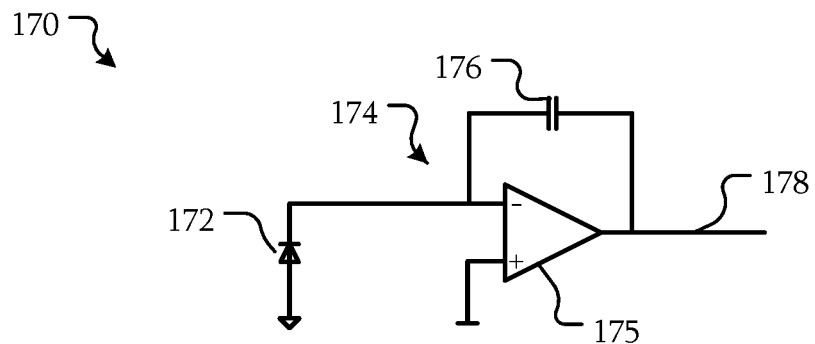
FIGS. 1C and 1D are examples of pixels of different types of detectors according to some embodiments.

The integrating detector 102 includes multiple pixels 170, each of which are configured to integrate signal from incident photons from radiation 108. Referring to FIGS. 1A and 1C an example of a pixel 170 of an integrating detector 102 is illustrated. In this example, the pixel 170 of the integrating detector 102 includes a photodetector 172 and an integrator circuit 174 having an integrated output 178 with an amplifier 175 and a storage capacitor 176 on which a charge is integrated for each photon. Switching circuitry may also be included to control when charge from the photodetector 172 is integrated and readout. While an example of a pixel 170 in an integrating detector 102 has been illustrated, other circuits may be used to integrate the signal from the incident photons, including integrating the signal on the capacitance of the photo-diode itself. Amplifiers, analog-to-digital converters, row and column circuitry, or the like may be present to generate an image 152.

Radiation 108, such as x-ray beams, may have a spectrum of energy where the energy is not concentrated at any one energy level. As a result, the incident photons may have different individual energy levels. Once the signal from two or more photons is integrated in a pixel 170 of the integrating detector 102, the energy level of each photon and the peak energy level may be lost. Without a count of the number of individual photons, the average energy may also be lost.

The energy sensing detector 104 is configured to generate energy information 154 in response to the radiation 108. The energy information 154 may represent the energy of each photon, whether the energy of the photon is within one of multiple energy ranges, the average energy of multiple photons, the peak energy of multiple photons, an energy distribution of multiple photons, a combination of such or similar information, or the like. For example, the energy sensing detector may both count the number of photons and integrate signal from each photon. The combination of the count and the integrated signal may provide a value indicative of the average energy of the photons. In another example, the energy sensing detector 104 may include a plurality of sensors, each configured to sense a particular range of energies. Each of the sensors may be disposed to receive incoming photons through a filter that filters out photons outside of the associated range. The energy sensing detector 104 or subsequent processing may convert the signal from the sensors into an average energy level. In some embodiments, the energy sensing detector 104 may include one or more scintillators to convert incoming x-ray photons to optical wavelengths and optical sensors configured to sense those converted photons. Each of the above examples, combinations of these examples, or the like may be part of the energy information 154.

Figure 1D:
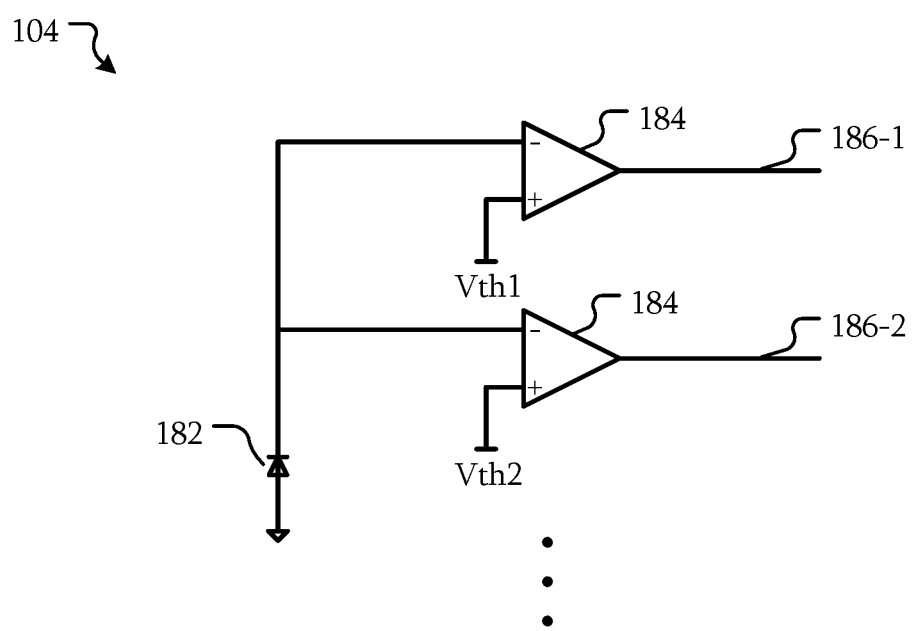

Referring to FIGS. 1A and 1D, an example of an energy sensing detector 104 is illustrated. The energy sensing detector 104 includes a photodetector 182 and multiple comparators 184. Each of the comparators may be configured to compare a signal from the photodetector 182 to an associated threshold Vth (e.g. Vth1 and Vth2) to generate a comparison result 186 (e.g. 186-1 and 186-2). The thresholds Vth may be set to divide the signal from the photodetector 182 into multiple bins. The multiple comparison results 186 may be converted into the energy information 154. Other circuitry, such as counters, switching circuits, amplifiers, or the like may also be included. In other embodiments, the energy sensing detector 104 may include different circuitry and may be configured to provide one or more of the types of energy information 154 described above. Although one example of an energy sensing detector 104 has been illustrated, the energy sensing detector 104 may be a variety of detectors.

Imagers having a matrix of energy sensing detectors such as the energy sensing detector 104 described above may be relatively expensive when compared with imagers based on integrating detectors 102 of similar size. As a result, any system formed with energy sensing detectors 104 alone may be significantly more expensive or significantly smaller in size. However, by including one or more energy sensing detectors 104 as described herein, energy information 154 of the energy of the photons may still be used to improve processing of an image 152 without the significant increase in cost of using a full energy sensing detector array.

In some embodiments, the energy sensing detector 104 may be a direct converting detector, such as a photoconducting material that converts x-rays directly to electrical charge. Such a direct converting detector would not have a scintillator. In other embodiments, an energy sensing detector 104 may include a dedicated scintillator, multiple pixels of an energy sensing detector 104 may include a dedicated scintillator, each pixel of an energy sensing detector 104 may include a dedicated scintillator, or the like. In some embodiments, the integrating detector 102 and the energy sensing detector 104 may share a scintillator. In FIG. 1A, scintillator 113 is illustrated as an example of a shared scintillator; however, in other embodiments, the scintillator 113 may only be used with the integrating detector 102.

Referring to FIGS. 1A and 1B, the pixels 170 of the integrating detector 102 may be disposed on one or more layers of the integrating detector 102. The integrating detector 102 may be a front-side illuminated or back-side illuminated detector. The energy sensing detector 104 overlaps with the pixels 170 of the integrating detector 102 with respect to the incoming radiation 108. That is, if radiation 108 is incident across the integrating detector 102, some of that radiation 108 will be incident on the energy sensing detector 104. Although the energy sensing detector 104 may be disposed at a center of the integrating detector 102, in other embodiments the energy sensing detector 104 may be in a different position, but still overlapping the pixels 170 of the integrating detector 102. The energy sensing detector 104 is disposed on a side of the integrating detector 102 opposite to the incident radiation 108. In some embodiments, the energy sensing detector 104 may be disposed on or attached to the integrating detector 102; however, in other embodiments, the energy sensing detector 104 may be disposed in a different location but still in the path of the radiation 108. For example, as will be described below, the energy integrating detector 104 may be disposed on an opposite side of the integrating detector 102, within the same enclosure as the integrating detector 102, or the like.

The integrating detector 102 may be configured to generate the image 152 based on signal received by the pixels 170. The energy sensing detector 104 may be configured to generate the energy information 154 associated with an energy of photons, such as an energy distribution of x-ray photons, an average energy of the photons, a peak energy of the photons, or the like as described above. Each image 152 is associated with a corresponding set of data from the energy sensing detector 104. In particular, that set of energy information 154 from the energy sensing detector 104 is data generated during an acquisition period for the image 152. While the image 152 and the energy information 154 are illustrated as being separate, in some embodiments, the image 152 may be combined with the energy information 154. For example, the energy information 154 may be part of meta-data of the image 152.

In some embodiments, the detector 101 is coupled to a processor 106. The processor is coupled to a memory 107. The processor 106 may include a general purpose processor, a digital signal processor (DSP), an application specific integrated circuit, a microcontroller, a programmable logic device, discrete circuits, a combination of such devices, or the like. The processor 106 may include internal portions, such as registers, cache memory, processing cores, or the like, and may also include external interfaces, such as address and data bus interfaces, interrupt interfaces, or the like. Although only one processor 106 is illustrated in the imaging system 100a, multiple processors 106 may be present. In addition, other interface devices, such as readout circuitry, logic chipsets, hubs, memory controllers, communication interfaces, or the like may be part of the imaging system 100a to connect the processor 106 to internal and external components. In particular, readout circuitry, frame buffers, or other circuitry configured to process an image from the integrating detector 102 may be coupled between the processor 106 and the integrating detector 102 to provide the image 152 to the processor 106. In some embodiments, one or more of such components may be disposed on the perimeter of the integrating detector 102.

The memory 107 may include a dynamic random access memory (DRAM) module, a double data rate synchronous dynamic random access memory (DDR SDRAM) according to various standards such as DDR, DDR2, DDR3, DDR4, static random access memory (SRAM), non-volatile memory such as Flash, spin-transfer torque magentoresistive random access memory (STT-MRAM), or Phase-Change RAM, magnetic media, or the like.

In some embodiments, the processor 106 and memory 107 are part of the imaging system 100a. Accordingly, the imaging system 100a may be configured to output an adjusted image based on an energy of the incident radiation 108. In some embodiments, the processor 106 is configured to output adjusted images in real time. That is, before or while a subsequent image is being acquired by the integrating detector 102, the processor 106 is configured to output the adjusted image 156. In other embodiments, a sequence of images 152 and a corresponding sequence of energy information 154 may be output and stored in the memory 107 for later processing.

In some embodiments the processor 106 and memory 107 may be part of a separate system. However, as the image 152 from the integrating detector 102 and the energy information 154 from the energy sensing detector 104 are available, the image 152 may still be adjusted as described herein by the separate system.

Figure 2C:
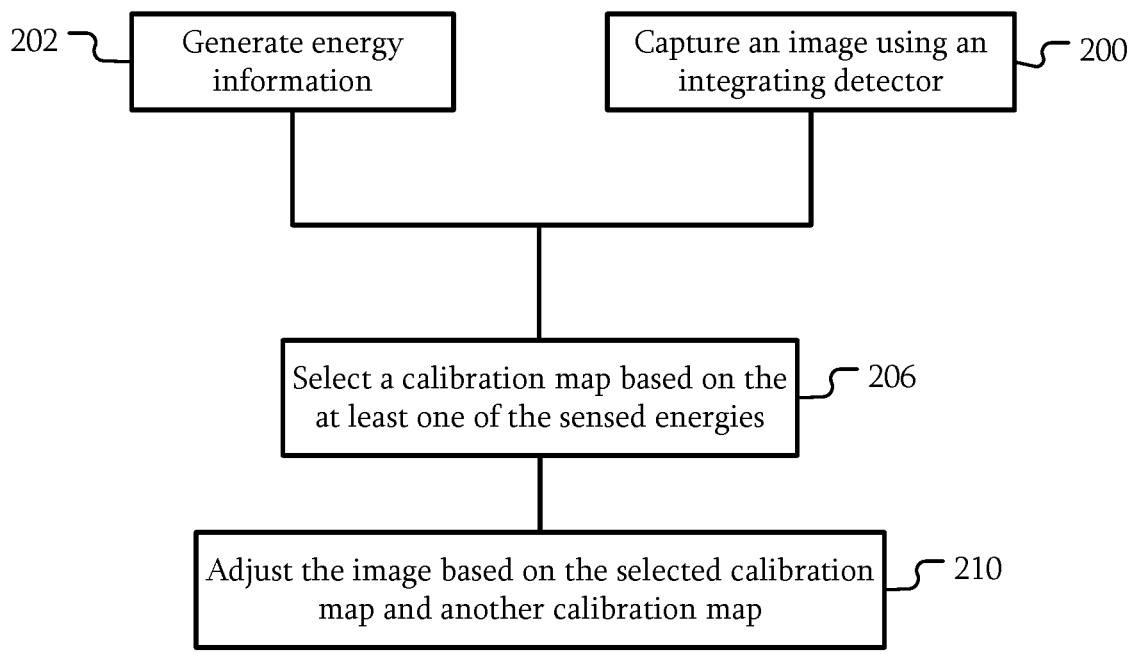

FIGS. 2A-2E are flowcharts illustrating operation an imaging system according to some embodiments. Referring to FIGS. 1A, 1B, and 2A, in some embodiments, in 200 an image is captured using the integrating detector 102. For example, the imaging system 100a may be illuminated with an x-ray beam 108 with a patient or specimen in the path of the beam. The pixels of the integrating detector 102 integrate signal in response to incident photons or associated optical photons from a scintillator. The integrated results over the acquisition period may be read from the pixels using readout circuitry to generate a 2D image 152.

In 202, the energy information 154 is generated by the energy sensing detector 104 during the acquisition period. That is, at the same time the image 152 is being acquired by the integrating detector 102, the energy sensing detector 104 is sensing photons from the same incident beam 108. Thus, the generated energy information 154 is related to the energy of photons used during the acquisition of the image by the integrating detector 102. In some embodiments the energy information 154 includes information on energy of photons only during the acquisition period. That is the energy information 154 may not be associated with multiple images 152. Rather, each image 152 is associated with a separately generated energy information 154. However, in other embodiments, the energy information 154 may include information from acquisition periods of multiple images 152.

In 204, the image 152 is adjusted based on the associated energy information 154. For example, the energy information 154 from the energy sensing detector 104 may include an average energy per photon, a peak energy, an energy distribution, or the like. In some embodiments, the processor 106 is configured to receive the energy information 154 in a variety of forms and convert the energy information 154 into the average, peak, and/or distribution of energies of the photons acquired during the acquisition period; however, in other embodiments, the energy information 154 itself may include the average, peak, and/or distribution of energies. The processor 106 may be configured to receive the image 152 and the energy information 154 and, in response, generate an adjusted image 156. The image 152 may be adjusted in a variety of ways, examples of which will be described in further detail below.

Referring to FIGS. 1A, 1B, and 2B, in some embodiments, the operations in 200 and 202 may be similar to those described above. However, in 206, a calibration map is selected from multiple calibration maps based on the energy information 154 from the energy sensing detector 104. For example, multiple calibration maps for the integrating detector 102 may be available. The calibration maps may be stored in the memory 107. The calibration maps may be associated with different energy levels. In some embodiments, each of the calibration maps may be associated with a different peak energy level. In other embodiments, each of the calibration maps may be associated with a different average energy level.

Each calibration map may include gain values, offsets, or the like for the pixels of the integrating detector 102. To generate the calibration maps, a calibration procedure may be performed on the imaging system 100a. For example, a beam 108 with a calibrated energy level, whether average, peak, distribution, or the like, may by used to generate a calibration map to be associated with that calibrated energy level.

In some embodiments, the calibration map with the closest average, peak, or distribution of energy may be used. In some embodiments, the closest may mean the closest in a linear function of energy while in other embodiments, the closest may be based on a non-linear function between the sensed energy and the energy levels associated with the calibration maps.

The selected calibration map may then be applied to the image 152 to generate an adjusted image 156. If a fixed calibration map generated at a single energy level was used, at different beam energy levels, image artifacts may be created in the adjusted image when the actual energy level departs from that associated with the calibrated energy level. These artifacts may lead to a lower image quality, mistakes in medical diagnoses, or the like. By selecting a calibration map based on the energy information 154, such artifacts may be reduced or eliminated. Even if a closest energy level match is used to select a calibration map, the quality of the adjusted image 156 may still be improved relative to a fixed calibration map for all energies.

Referring to FIGS. 1A, 1B, and 2C, in some embodiments, the operations in 200, 202, and 206 may be similar to those described above. However, in 210, the image 152 is adjusted based on the selected calibration map and at least one other calibration map of the calibration maps. For example, a second calibration map may be selected to be used in combination with the first selected calibration map to generate a new calibration map for adjusting the image. In some embodiments, the two calibration maps may be used to interpolate or extrapolate the new calibration map based on the energies of the selected calibration maps and the sensed energy from the energy sensing detector 104. As a result, the new calibration map may more closely approximate the calibration for the imaging system 100a had that calibration been performed at the specifically sensed energy level. Although using two calibration maps has been used as an example, in other embodiments more calibration maps may be used, such as by using three or more to generate a function representing a relationship between a particular energy and a composite calibration map.

Figure 2D:
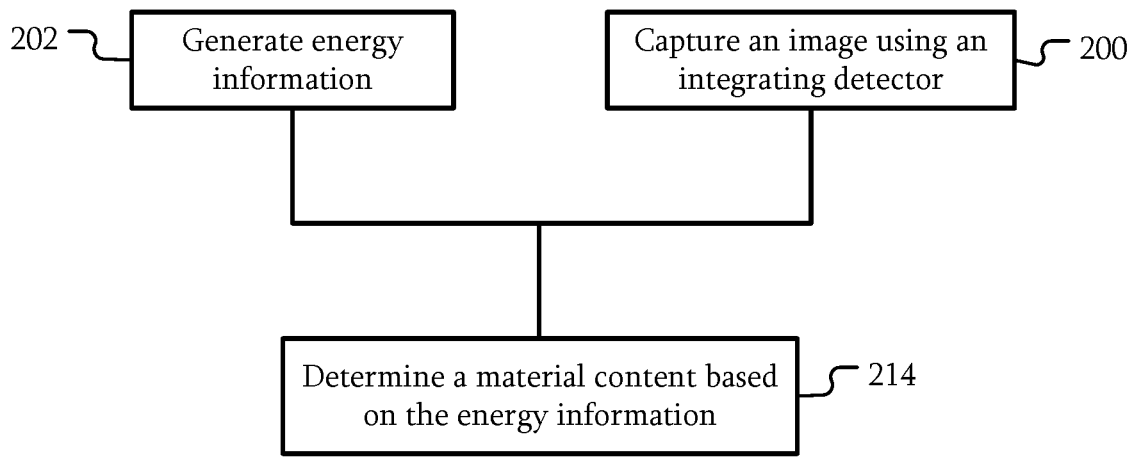

Referring to FIGS. 1A, 1B, and 2D, in some embodiments, the operations in 200 and 202 may be similar to those described above. However, in 214, a material content of a patient or specimen may be determined based on the energy information 154 generated by the energy sensing detector 104. For example, energy distribution information from the sensors can be used to determine the material content of an object in the path of an illuminating beam. In some embodiments, the energy sensing detector 104 may generate a spectrum of the incident energy. For example, the energy sensing detector 104 maybe configured to generate a spectrum in 1 kiloelectron-volts (keV) steps. That spectrum may be compared with a spectrum of the original beam and a type of material may be determined based on the comparison. Although 1 keV has been used as an example, in other embodiments, the steps may be different may be smaller or larger. For example, the steps may be about 500 electron-volts (eV).

In some embodiments, a comparison between energy information 154 generated by the energy sensing detector 104 over two exposures may be used to determine a material content. For example, an image may be acquired along with an energy from the energy sensing detector 104. The image 152 may have lighter or darker areas than the one corresponding to the energy sensing detector 104. The object may be moved such that the energy sensing detector 104 is sensing energy passing through a different portion of the object, such as one that resulted in the lighter or darker area in the image 152. Another exposure may be performed, resulting in another energy from the energy sensing detector. A material of the object may be determined based on a comparison of the energy measurements in the different positions. In some embodiments, the energy level or levels may be combined with an output of one or more pixels of the integrating detector 102 that overlap the energy sensing detector 104.

Figure 2E:
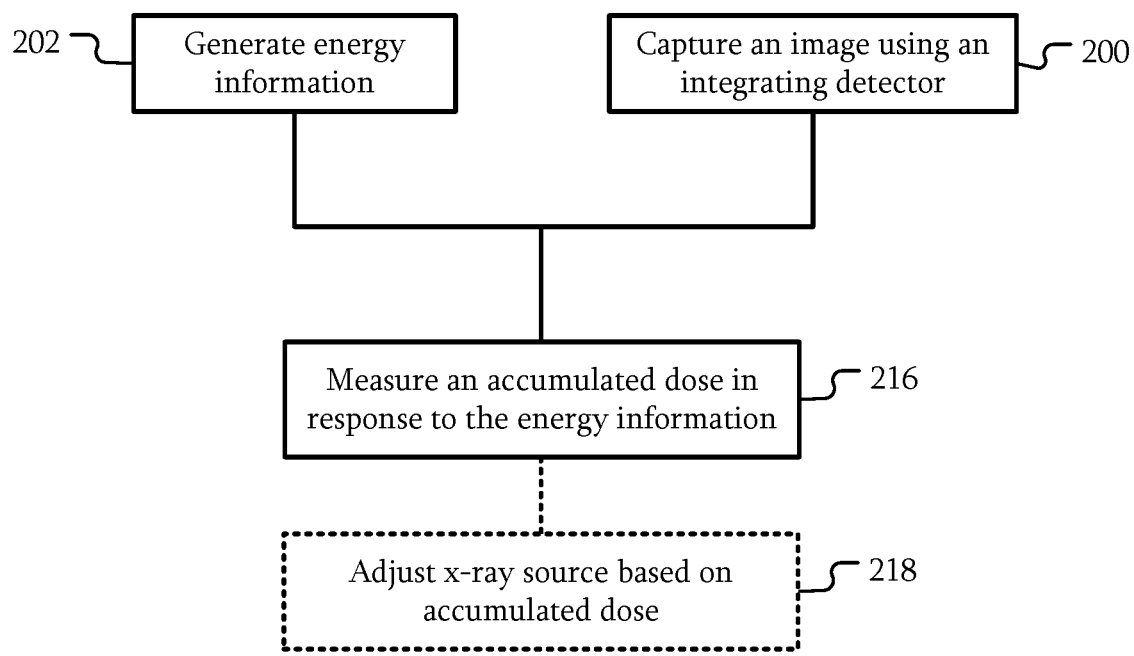

Referring to FIGS. 1A, 1B, and 2E, in some embodiments, the operations in 200 and 202 may be similar to those described above. However, in 216, an accumulated dose may be measured based on the energy information generated by the energy sensing detector 104. For example, the energy sensing detector 104 may be configured to sense a spectrum of the energy that has passed through an object. That spectrum may be compared with the spectrum of the incident illumination to determine what has been absorbed by the object. The absorbed amount may be added to an accumulated dose from frame to frame. Moreover, the accumulated dose may be reported in real-time on a frame-by-frame basis while images and/or video are being acquired.

Figure 3:
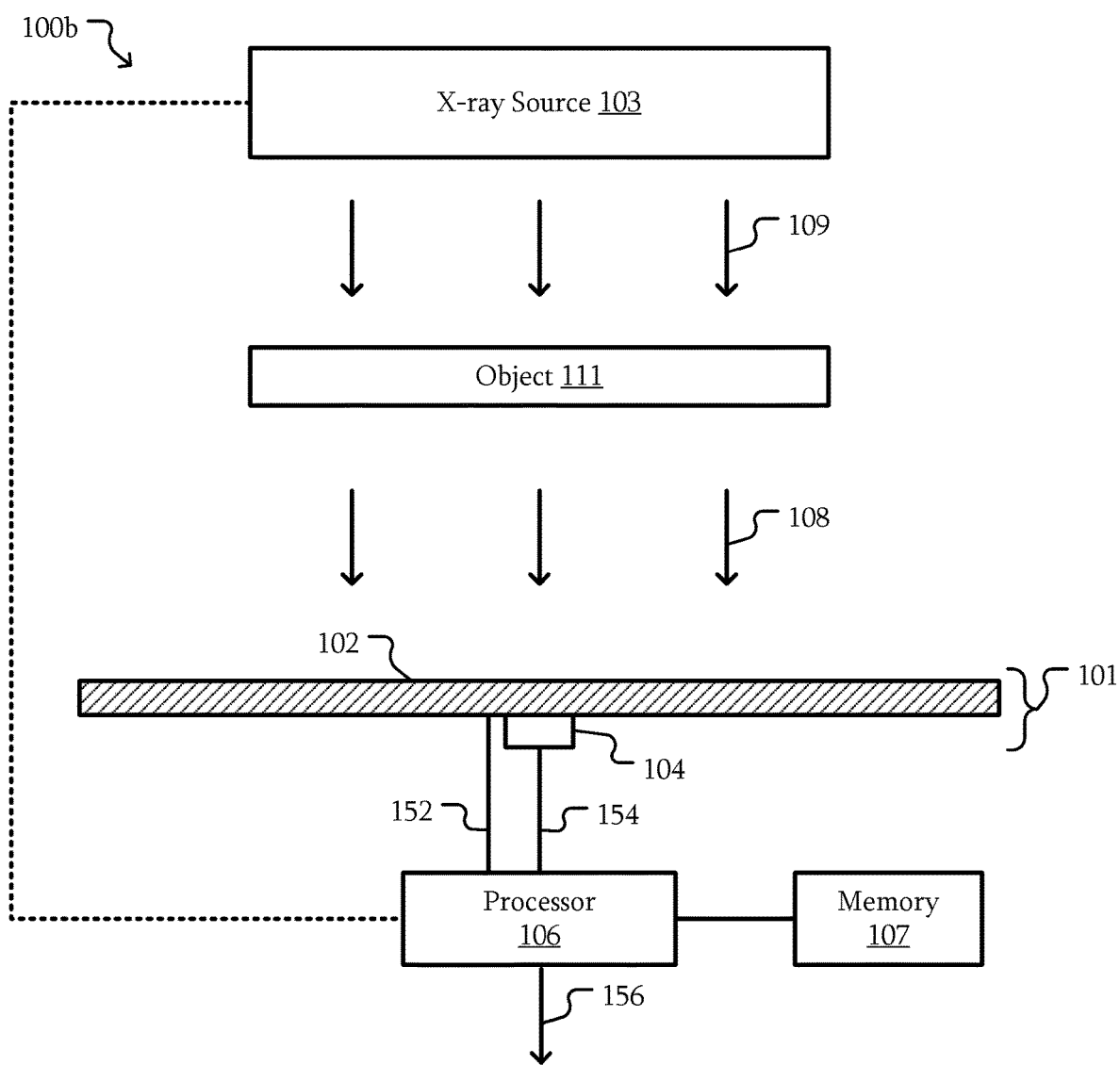
FIG. 3 is a block diagram of an imaging system according to some other embodiments.

FIG. 3 is a block diagram of an imaging system 100b according to some other embodiments. The imaging system 100b may be similar to the imaging systems 100 described herein. The imaging system 100b includes an x-ray source 103 configured to generate x-rays 109 directed towards the detector 101. An object 111 is disposed in the path of the x-ray beam 109. X-ray beam 108 represents the x-ray beam 109 as filtered by the object 111. The x-ray source 103 is coupled to the processor 106. As described above, although a single processor 106 is illustrated, the control of the x-ray source 103 may be implemented by a distributed control system including multiple processors, communication links (e.g., physical connections and/or wirelessly), or the like.

In some embodiments, the processor 106 may be configured to control the x-ray source 103. In particular, the processor 106 may be configured to adjust an intensity of the x-ray beam 109 in response to the energy sensing detector 104. For example, the energy sensing detector 104 may be used to perform an automatic brightness control (ABC) of the x-ray source 103. The energy sensing detector 104 may output energy information 154 related to the energy of the incident x-ray beam 108, such as the spectrum. The energy information 154 may be used to determine if the image 152 is relatively bright, such as when a structure of the object 111 absorbs a relatively smaller portion of the x-ray beam 109. The processor 106 may be configured to reduce the brightness of the x-ray source 103 accordingly. Similarly, when the energy information 154 indicates that a relatively larger portion of the x-ray beam 109 is being absorbed, the brightness may be increased. This change may occur on a frame-to-frame or pulse-to-pulse basis.

In some embodiments, the combination of the x-ray source 103 and detector 101 may not need to be calibrated during manufacturing or in the field. For example, the detector 101 need not be calibrated within the context of the entire imaging system 100b as the detector 101 and the subsequent processing in the processor 106 may accommodate variations in energy levels. If the calibration maps that are specific to the detector 101 are generated, when that detector 101 is paired with an x-ray source 103, the availability of the energy information 154 may be used to adjust the image 152 generated by the integrating detector 102. The energy of the incident x-ray beam 108 may vary due to variation in the operation of the x-ray source 103, an automatic brightness control procedure, or the like. However, as the energy information 154 is available, the image 152 may be adjusted as described herein.

Referring to FIGS. 2E and 3, in some embodiments, the measured dose may be used to adjust the x-ray source 103. As described above, an accumulated dose may be measured in 216. In 218, the x-ray source 103 may be adjusted based on the accumulated dose. For example, if the accumulated dose exceeds a threshold, such as about 1 microgray (μGy), the processor 106 may disable the x-ray source 103. In other embodiments, the intensity of the x-ray source 103 may be increased or decreased based on the accumulated dose. For example, the intensity may be adjusted to optimize beam 108 or 109 quality.

Figure 4A:
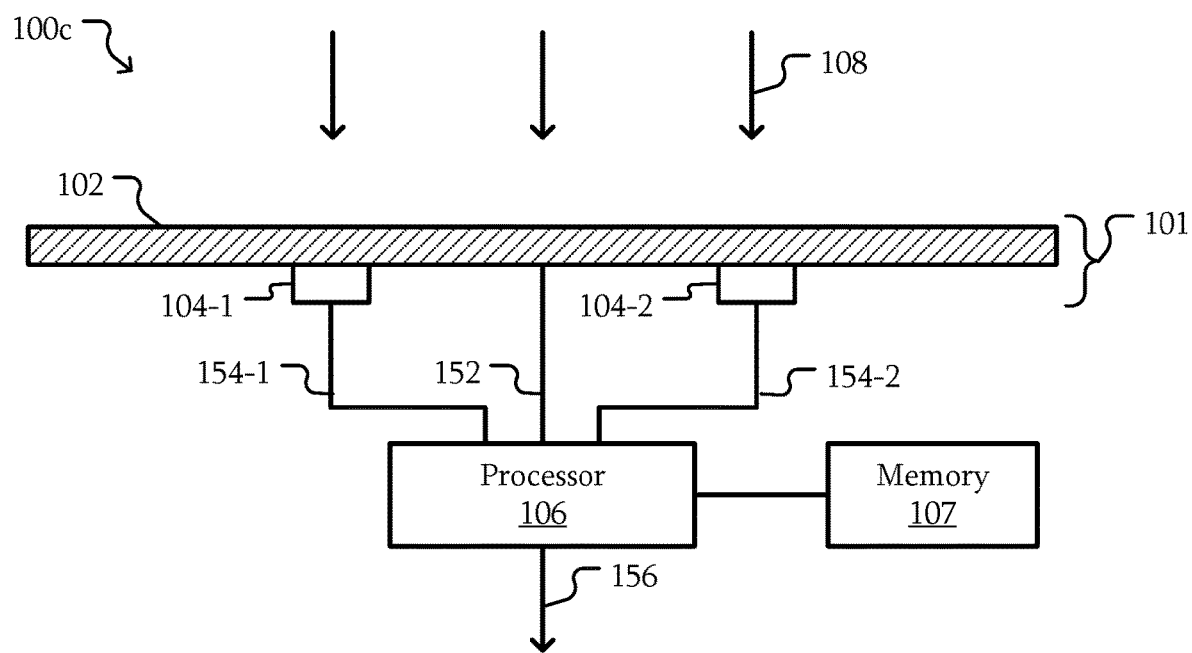
FIG. 4A is a block diagram of an imaging system with multiple backside energy detectors according to some embodiments.
Figure 4B:
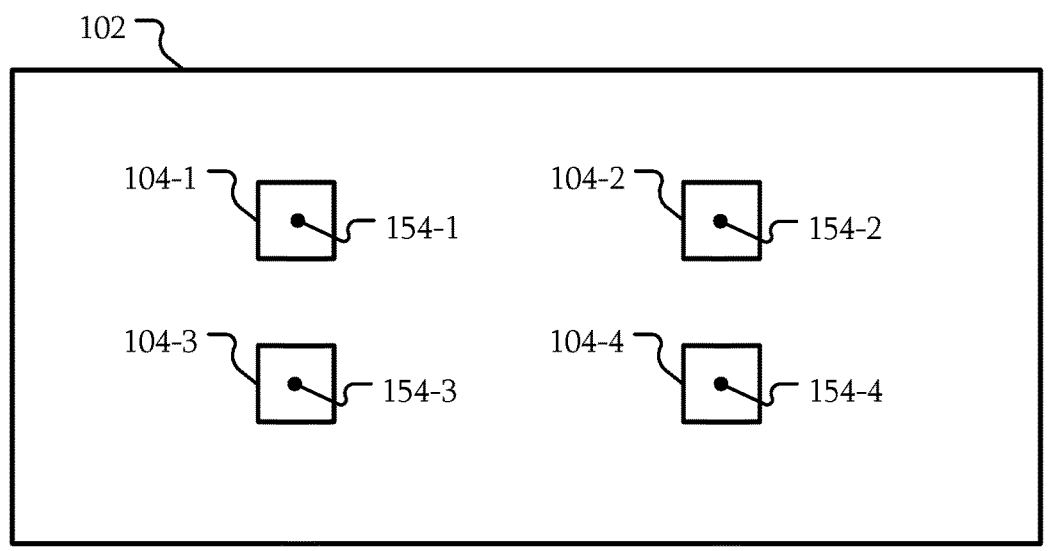
FIG. 4B is a plan view of detectors of the imaging system of FIG. 4A according to some embodiments.

FIG. 4A is a block diagram of an imaging system 100c with multiple backside energy detectors according to some embodiments. FIG. 4B is a plan view of detectors of the imaging system 100c of FIG. 4A according to some embodiments. Referring to FIGS. 4A and 4B, the imaging system 100c may be similar to the imaging systems 100 described herein. However, the imaging system 100c includes multiple energy sensing detectors 104 disposed on the integrating detector 102 and configured to sense the energy of each of a plurality of photons. Here four energy sensing detectors 104-1 to 104-4 are illustrated; however, any number may be present. However, in some embodiments, a resolution of the energy sensing detectors 104 may be less than that of the integrating detector 102.

The energy sensing detectors 104-1 to 104-4 are each overlapping the integrating detector 102 with respect to the radiation 108. Here, the energy sensing detectors 104-1 to 104-4 are disposed in an array. However, in other embodiments, the energy sensing detectors 104 may be disposed in a different layout overlapping the integrating detector 102.

The operation of the imaging system 100c may be similar to those described above. In some embodiments, the energy information 154-1, 154-2, 154-3, and 154-4 (collectively 154-1 to 154-4q from the energy sensing detectors 104-1, 104-2, 104-3, and 104-4 (collectively 104-1 to 104-4) may be combined to adjust the image 152, select a calibration map, determine a material, measure a dose, or the like. For example, the energy information 154-1 to 154-4 from the energy sensing detectors 104-1 to 104-4 may be aggregated to generate an average energy, peak energy, minimum energy, energy spectrum, or the like. The value may be used as described above.

In other embodiments, the energy information 154-1 to 154-4 from the energy sensing detectors 104-1 to 104-4 may be used in combination with the image 152 to select a calibration map. For example, the energy sensing detectors 104-1 to 104-4 may be used to determine the average energy of a dark portion of the image and the average energy of a lighter portion of the image. Based on a set of pairs of average energy and image value, portions of different calibration maps may be selected for different regions of the image, different pixels of the image, or the like. Although particular techniques of combining energy information 154-1 to 154-4 have been described above, in other embodiments, the energy information 154-1 to 154-4 may be combined in different ways and used to adjust the image 152.

Figure 5A:
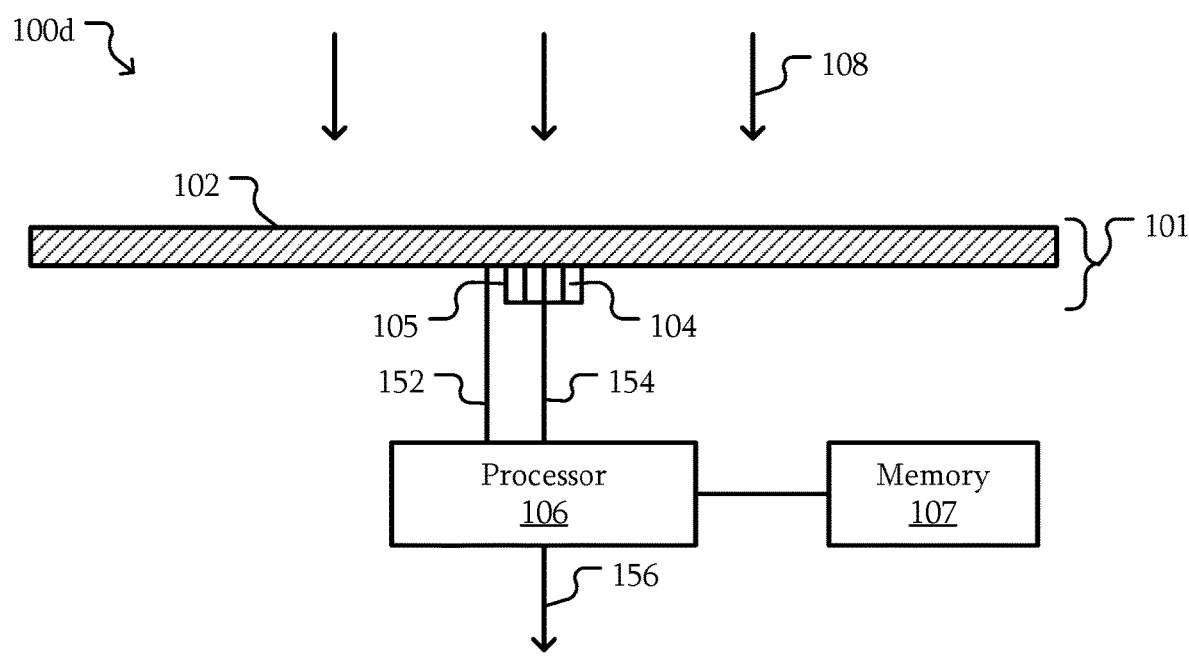
FIG. 5A is a block diagram of an imaging system with an energy detector array according to some embodiments.
Figure 5B:
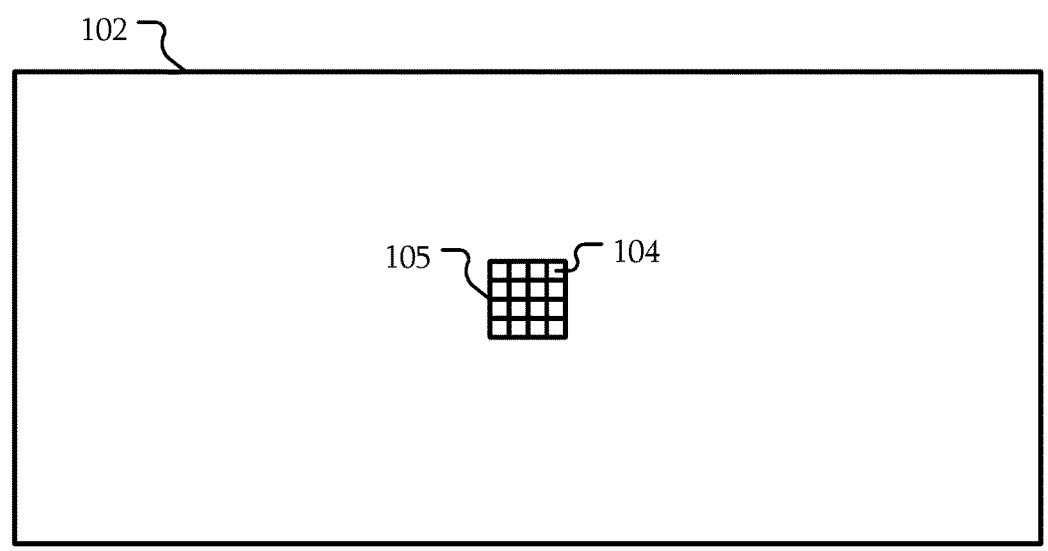
FIG. 5B is a plan view of detectors of the imaging system of FIG. 5A according to some embodiments.

FIG. 5A is a block diagram of an imaging system 100d with an energy detector array according to some embodiments. FIG. 5B is a plan view of detectors of the imaging system 100d of FIG. 5A according to some embodiments. Referring to FIGS. 5A and 5B, the imaging system 100d may be similar to the imaging systems 100 described herein.

However, in some embodiments, the imaging system 100d includes multiple energy sensing detectors 104 disposed in an energy sensing detector array 105. The multiple energy sensing detectors 104 of the energy sensing detector array 105 may be operated similarly to the discrete energy sensing detectors 104 described above.

In addition, the energy sensing detector array 105 may also be configured to generate an image based on the energy information. While the energy sensing detector array 105 may be smaller than the integrating detector 102, an object may be moved such that a region of interest is in the path of the beam 108 incident on the energy sensing detector array 105.

Figure 6A:
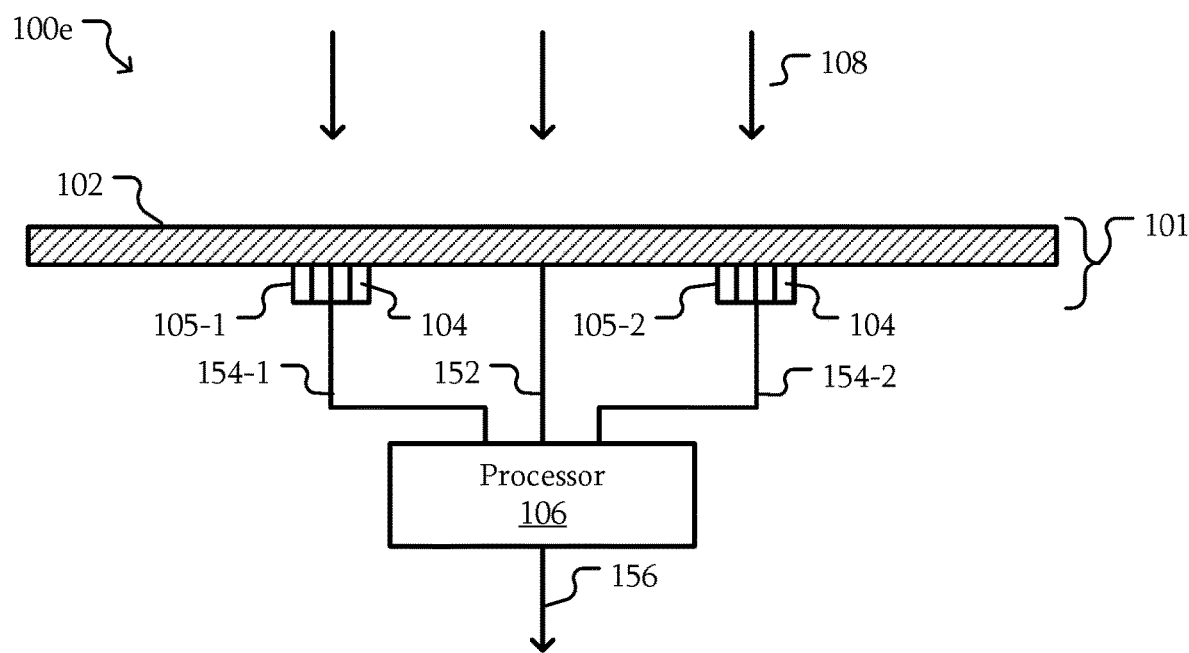
FIG. 6A is a block diagram of an imaging system with multiple energy detector arrays according to some embodiments.
Figure 6B:
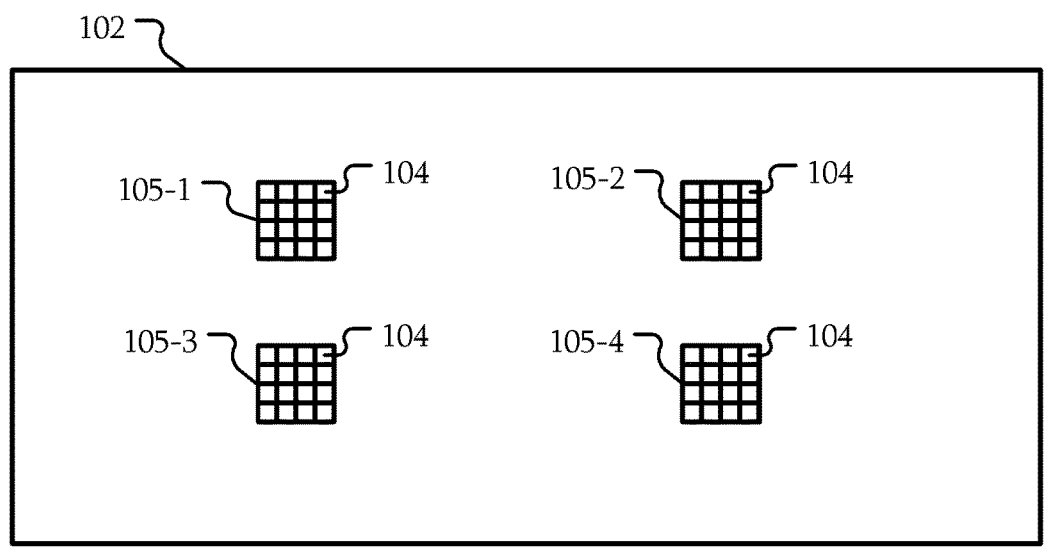
FIG. 6B is a plan view of detectors of the imaging system of FIG. 6A according to some embodiments.

FIG. 6A is a block diagram of an imaging system 100e with multiple energy detector arrays according to some embodiments. FIG. 6B is a plan view of detectors of the imaging system 100e of FIG. 6A according to some embodiments. The imaging system 100e may be similar to the imaging systems 100 described herein. However, in some embodiments, multiple energy sensing detector arrays 105 may be disposed on the integrating detector 102 and operated similarly to the single energy sensing detector array 105 and similar to the multiple discrete energy sensing detectors 104.

Figure 7:
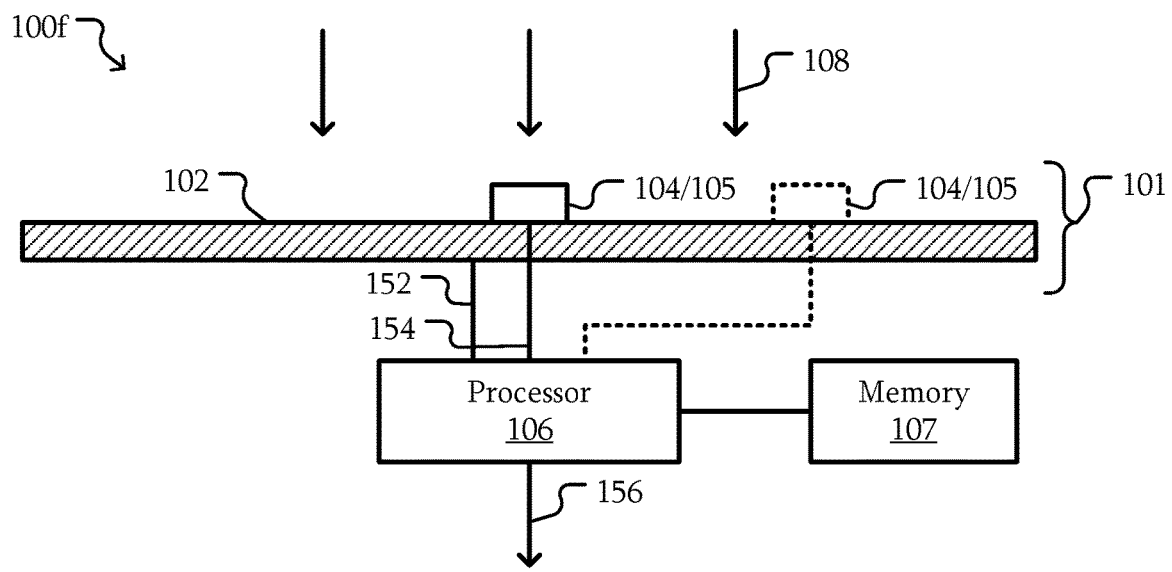
FIG. 7 is a block diagram of an imaging system with one or more front side energy sensing detectors according to some embodiments.

FIG. 7 is a block diagram of an imaging system 100f with one or more front side energy sensing detectors 104 according to some embodiments. The imaging system 100f may be similar to the imaging systems 100 described herein. However, in some embodiments, the energy sensing detector or detectors 104 or the energy sending detector array or arrays 105 may be disposed in front of the integrating detector 102. Back side refers to a side of the detector 101 opposite the incident radiation 108, and front side refers to a side of the detector 101 that receives the incident radiation 108. As described above, the energy sensing detectors 104 or arrays 105 may be disposed on a back side of the integrating detector 102. However, if the energy sensing detectors 104 or arrays 105 result in a negligible or correctible shadow on the integrating detector 102, the energy sensing detectors 104 or arrays 105 may be disposed on the front side of the detector 101 between the incoming radiation 108 and the integrating detector 102.

Figure 8:
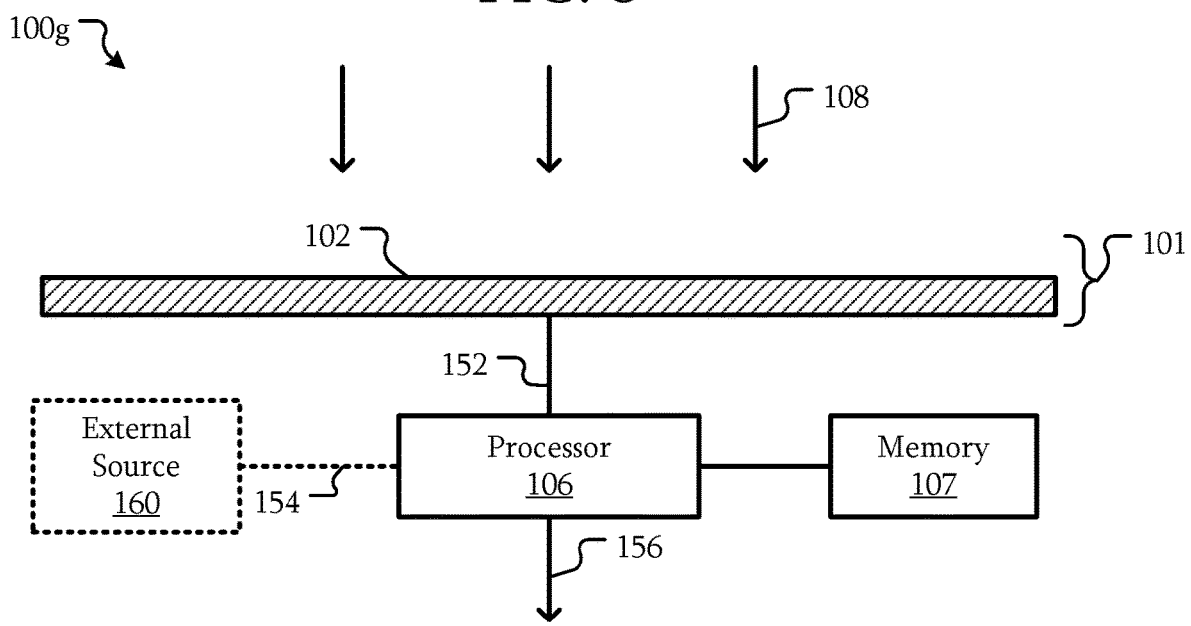
FIG. 8 is a block diagram of an imaging system with an external input according to some embodiments.

FIG. 8 is a block diagram of an imaging system 100g with an external input according to some embodiments. The imaging system 100g may be similar to the imaging systems 100 described herein; however, the imaging system 100g does not have an energy sensing detector 104. Instead the processor 106 is configured to receive the energy information 154 from an external source 160. The external source may include an energy sensing detector that is a component of a larger system, information related to a calibrated output of an illuminating source, or the like. Regardless, the energy information 154 still represents the energy of the photons as described above. The processor 106 may still be configured to output an adjusted image 156 based on the externally generated energy information 154.

Figure 9:
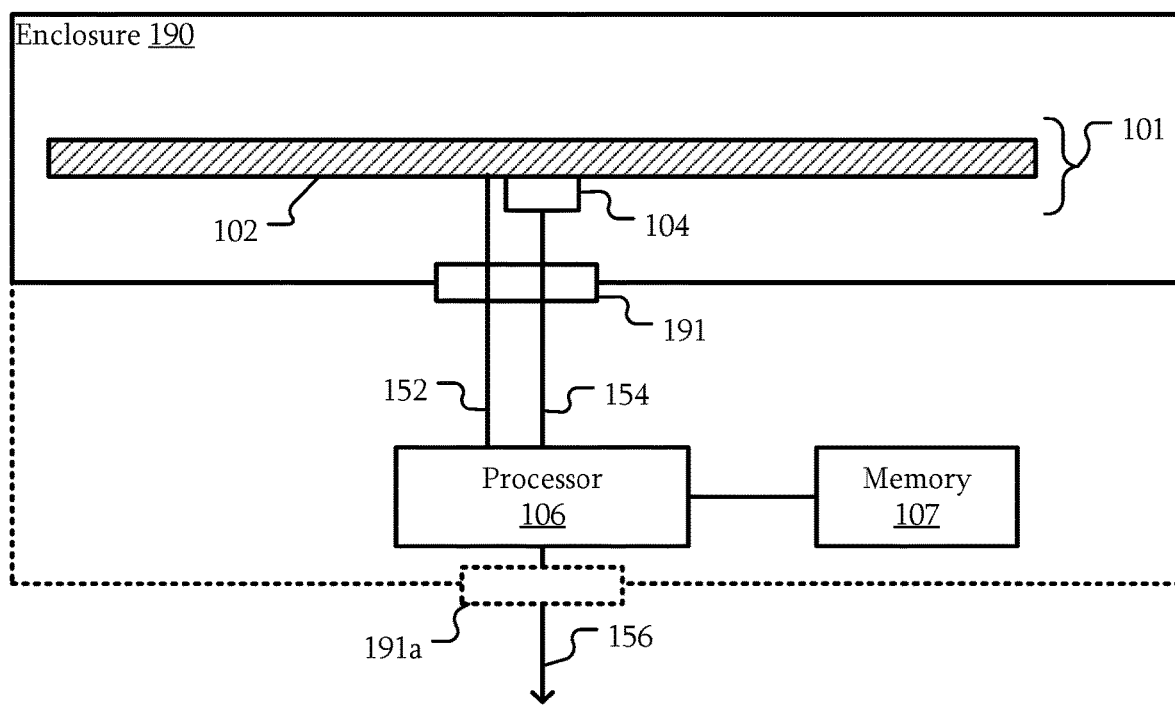
FIG. 9 is a block diagram of an imaging system according to some embodiments.

FIG. 9 is a block diagram of an imaging system 100h according to some embodiments. The imaging system 100h may be similar to the imaging systems 100 described herein. However, the imaging system 100h includes an enclosure. The detector 101 including the integrating detector 102 and the energy sensing detector 104 are disposed in the enclosure. The enclosure 190 may include a housing, case, frame, or the like to contain the detector 101. The enclosure 190 may include an opening, a wall with low absorption for the radiation 108, or the like to allow the radiation 108 to illuminate the detector 101.

The enclosure 190 includes a communication interface 191. The communication interface 191 is an interface through which the image 152 and the energy information 154 may be communicated to the processor 106. For example, the communication interface 191 may include a serial interface, a parallel interface, a network interface, a standardized communication interface such as universal serial bus (USB), peripheral component interconnect express (PCIe), nonvolatile memory express (NVMe), or the like.

Although the processor 106 and memory 107 are illustrated as being outside of the enclosure 190, in some embodiments, the processor 106 and memory 107 may be disposed within the enclosure 190. The adjusted image 156 may be output from the enclosure 190 through a communication interface 191a similar to the communication interface 190 described above.

In some embodiments, the imaging systems 100 described above may be part of a medical imaging system. In other embodiments, the imaging systems 100 may be part of a portable vehicle scanning system as part of a cargo scanning system. In other embodiments, the imaging systems 100 described above may be part of a non-destructive testing system. In other embodiments the imaging systems described above may be used in other applications.

Some embodiments include a system 100, comprising: an integrating detector 102 including a plurality of pixels, each pixel configured to integrate signal from photons of a radiation beam 108; and an energy sensing detector 104 overlapping the pixels of the integrating detector 102 and configured to generate energy information in response to the radiation beam 108.

Some embodiments include an enclosure 190; wherein the integrating detector 102 and the energy sensing detector 104 are disposed in the enclosure 190.

In some embodiments, the system 100 further comprises a processor 106 configured to: receive an image 152 from the integrating detector 102; and adjust the image 152 based on the energy information.

In some embodiments, the processor 106 is further configured to: select a calibration map from a plurality of calibration maps in response to the energy information; and adjust the image 152 based on the selected calibration map.

In some embodiments, the energy information comprises at least one of a mean energy, a peak energy, and an energy distribution of the radiation beam 108.

In some embodiments, the processor 106 is further configured to determine a material content based on the energy sensing detector 104.

In some embodiments, the processor 106 is further configured to measure an accumulated dose in response to the energy sensing detector 104.

In some embodiments, the energy sensing detector 104 is one of a plurality of energy sensing detectors 104, each configured to generate energy information in response to the radiation beam 108.

In some embodiments, the energy sensing detectors 104 are disposed in at least one energy sensing detector array 105.

In some embodiments, the system 100 further comprises: an x-ray source 103 configured to direct an x-ray beam 109 towards the integrating detector 102 and the energy sensing detector 104; wherein the x-ray source 103 is configured to adjust an intensity of the x-ray beam 109 in response to the energy sensing detector 104; and the radiation beam 108 comprises at least part of the x-ray beam 108.

In some embodiments, the energy sensing detector 104 is disposed on a side of the integrating detector 102 opposite to a side configured to receive the radiation beam 108.

Some embodiments include a method, comprising: illuminating an integrating detector 102 with a radiation beam 108; capturing an image 152 using the integrating detector 102 during an acquisition period; sensing energy information for the radiation beam 108 during the acquisition period; and adjusting the image 152 based on the energy information.

In some embodiments, the method further comprises: selecting a calibration map from a plurality of calibration maps based on the energy information; and adjusting the image 152 based on the selected calibration map.

In some embodiments, each of the calibration maps is associated with a different energy level.

In some embodiments, adjusting the image 152 based on the selected calibration map comprises adjusting the image 152 based on the selected calibration map and at least one other calibration map of the calibration maps.

In some embodiments, the method further comprises adjust the image 152 based on at least one of a mean energy, a peak energy, and an energy distribution of the radiation beam 108.

In some embodiments, sensing the energy information for the radiation beam 108 during the acquisition period comprises sensing energy information using a plurality of energy sensing detectors 104 during the acquisition period.

In some embodiments, the method further comprises determining a material content based on the energy sensing detector 104.

In some embodiments, the method further comprises to measuring an accumulated dose in response to the energy sensing detector 104.

Some embodiments include a system, comprising: means for generating an image by integrating signal from photons of a radiation beam; means for sensing energy information for the radiation beam; and means for adjusting the image in response to the energy information. Examples of the means for generating an image by integrating signal from photons of the radiation beam include the integrating detector 102 described above. Examples of the means for sensing energy information for the radiation beam include the energy sensing detectors 104, energy sensing detector arrays 105, and the external source 160 described above. Examples of the means for adjusting the image in response to the means for sensing energy of the photon include the processor 106 and memory 107 as described above.

In some embodiments, the system 100 further comprises: means for selecting a calibration map from a plurality of calibration maps in response to the energy information; wherein the means for adjusting the image comprises means for adjusting the image in response to a selected calibration map. Examples of the means for selecting a calibration map from a plurality of calibration maps include the processor 106 and memory 107 as described above.

Although the structures, devices, methods, and systems have been described in accordance with particular embodiments, one of ordinary skill in the art will readily recognize that many variations to the particular embodiments are possible, and any variations should therefore be considered to be within the spirit and scope disclosed herein. Accordingly, many modifications may be made by one of ordinary skill in the art without departing from the spirit and scope of the appended claims.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed to cover the corresponding structure, material, or acts described herein and equivalents thereof in accordance with 35 U.S.C. § 112 ¶6. Embodiments of the invention in which an exclusive property or privilege is claimed are defined as follows.

The invention claimed is:

1. A system, comprising:
an integrating detector including a plurality of pixels, each pixel of the plurality of pixels configured to integrate signal from photons of a radiation beam;
at least one energy sensing detector overlapping the plurality of pixels of the integrating detector and configured to generate energy information in response to the radiation beam; and
a processor configured to:
receive an image from the integrating detector;
select a calibration map from a plurality of calibration maps in response to the energy information; and
adjust the image based on the selected calibration map.

2. The system of claim 1, further comprising:
an enclosure;
wherein the integrating detector and the at least one energy sensing detector are disposed in the enclosure.

3. The system of claim 1, wherein the energy information comprises at least one of a mean energy, a peak energy, and an energy distribution of the radiation beam.

4. The system of claim 1, wherein the processor is further configured to determine a material content based on the energy information.

5. The system of claim 1, wherein the processor is further configured to measure an accumulated dose in response to the energy information.

6. The system of claim 1, wherein the at least one energy sensing detector comprises a plurality of energy sensing detectors, each energy sensing detector of the plurality of energy sensing detectors being configured to generate energy information in response to the radiation beam.

7. The system of claim 6, wherein the plurality of energy sensing detectors comprise at least one energy sensing detector array.

8. The system of claim 1, further comprising:
an x-ray source configured to direct an x-ray beam towards the integrating detector and the at least one energy sensing detector;
wherein:
the x-ray source is configured to adjust an intensity of the x-ray beam in response to the at least one energy sensing detector; and
the radiation beam comprises at least part of the x-ray beam.

9. The system of claim 1, wherein the at least one energy sensing detector is disposed on a side of the integrating detector opposite to a side of the integrating detector configured to receive the radiation beam.

10. The system of claim 1, wherein the at least one energy sensing detector is smaller in size than the integrating detector.

11. A method, comprising:
illuminating an integrating detector with a radiation beam;
capturing an image using the integrating detector during an acquisition period;
sensing energy information using at least one energy sensing detector for the radiation beam during the acquisition period;
selecting a calibration map from a plurality of calibration maps based on the energy information; and
adjusting the image based on the selected calibration map.

12. The method of claim 11, wherein adjusting the image based on the selected calibration map comprises adjusting the image based on the selected calibration map and at least one other calibration map of the plurality of calibration maps.

13. The method of claim 11, further comprising adjust the image based on at least one of a mean energy, a peak energy, and an energy distribution of the radiation beam.

14. The method of claim 11, wherein:
the at least one energy sensing detector comprises a plurality of energy sensing detectors.

15. The method of claim 11, further comprising determining a material content based on the energy information.

16. The method of claim 11, further comprising to measuring an accumulated dose in response to the energy information.

17. The method of claim 11, wherein the at least one energy sensing detector is smaller in size than the integrating detector.

18. A system, comprising:
means for generating an image by integrating signal from photons of a radiation beam;
means for sensing energy information for the radiation beam;
means for selecting a calibration map from a plurality of calibration maps in response to the energy information; and
means for adjusting the image in response to the selected calibration map.

19. The system of claim 18, wherein the means for sensing energy information is smaller in size than the means for generating the image.

20. A system, comprising:
an integrating detector including a plurality of pixels, each pixel of the plurality of pixels configured to integrate signal from photons of a radiation beam;
an energy sensing detector overlapping the plurality of pixels of the integrating detector and configured to generate energy information in response to the radiation beam, wherein the energy sensing detector is smaller in size than the integrating detector; and
a processor configured to:
receive an image from the integrating detector; and
adjust the image based on the energy information.

* * * * *